United States Patent
Salamone et al.

(10) Patent No.: US 7,300,768 B2
(45) Date of Patent: Nov. 27, 2007

(54) ENZYMATIC MEASUREMENT OF IMATINIB MESYLATE

(75) Inventors: Salvatore J. Salamone, Stockton, NJ (US); Jodi Blake Courtney, Doylestown, PA (US); Katherine Salamone, Stockton, NJ (US)

(73) Assignee: Saladax Biomedical Inc., Bethlehem, PA (US)

( * ) Notice: Subject to any disclaimer, the term of this patent is extended or adjusted under 35 U.S.C. 154(b) by 0 days.

(21) Appl. No.: 11/272,918

(22) Filed: Nov. 14, 2005

(65) Prior Publication Data

US 2006/0105421 A1    May 18, 2006

Related U.S. Application Data

(60) Provisional application No. 60/628,672, filed on Nov. 18, 2004.

(51) Int. Cl.
*C12Q 1/48* (2006.01)
(52) U.S. Cl. .................... 435/15; 435/194; 600/368
(58) Field of Classification Search ................ 435/15, 435/194
See application file for complete search history.

(56) References Cited

U.S. PATENT DOCUMENTS 6,599,711 B2 * 7/2003 Crouch et al. ................ 435/15
2003/0158105 A1 * 8/2003 Sawyers et al. ............... 514/12

OTHER PUBLICATIONS

-Foulkes et al. (1985) J Biol Chem 260, 8070-807.*
Parast et al. (Nov. 5, 1998) Biochem 37, 16788-16801.*
Schulte et al. (1999) Anal Biochem 269, 245-254.*
Parast CV et al (1998) Characterization and kinetic mechanism of catalytic domain of human vascular endothelial growth factor receptor-2 tyrosine kinase . . . Biochemistry 37: pp. 16788-16801.*
Gambacorti-Passerini CB et al (2002) Differences between in vivo and in vitro sensitivity to imatinib of bcr/abl cells obtained from leukemic patients. Blood Cells, Molecules and Diseases 28: pp. 361-372.*
Peralba JM et al (2003) Pharmacodynamic evaluation of CCI-779, an inhibitor of mTOR, in cancer patients. Clin Cancer Res 9: pp. 2887-2892.*
Foulkes JG et al (1985) Purification and characterization of a protein-tyrosine kinase encoded by abelson murine leukemia virus. J Biol Chem 260: pp. 8070-8077.*
The International Preliminary Report on Patentability by the International Bureau of WIPO, issued on May 31, 2007, in the PCT application No. PCT/US2005/041049.
Barker et al., Characterization of pp60c-src Tyrosine Kinase Activities Using a Continuous Assay: Autoactivation of the Enzyme Is an Intermolecular Autophosphorylation Process, Biochemistry, 34:14843-14851 (1995).
Kurzrock et al., Philadelphia Chromosome—Positive Leukemias: From Basic Mechanisms to Molecular Therapeutics, Annals of Internal Medicine, 138(10):819-831 (May 20, 2003).

* cited by examiner

*Primary Examiner*—Jon Weber
*Assistant Examiner*—Clark D Petersen

(57) ABSTRACT

The present invention provides a method for the enzymatic measurement of protein tyrosine kinase inhibitors in biological samples. The present invention also provides assay reagents and packaged kits useful for performing enzymatic measurement of imatinib mesylate and other bcr-abl protein kinase inhibitors in biological samples.

17 Claims, No Drawings

ENZYMATIC MEASUREMENT OF IMATINIB MESYLATE

CROSS-REFERENCE TO RELATED APPLICATION

This Application claims the benefit of Provisional Application Ser. No. 60/628,672 filed Nov. 18, 2004.

FIELD OF THE INVENTION

This invention relates to the field of enzymatic assays for determining the presence and/or quantifying the amount of imatinib or its pharmacologically active metabolites in human biological fluids in order to rapidly determine optimal drug concentrations during chemotherapy.

BACKGROUND OF THE INVENTION

Cancer is a term used to describe a group of malignancies that all share the common trait of developing when cells in a part of the body begin to grow out of control. Most cancers form as tumors, but can also manifest in the blood and circulate through other tissues where they grow. Cancer malignancies are most commonly treated with a combination of surgery, chemotherapy, and/or radiation therapy. The type of treatment used to treat a specific cancer depends upon several factors including the type of cancer malignancy and the stage during which it was diagnosed.

Imatinib has the following formula:

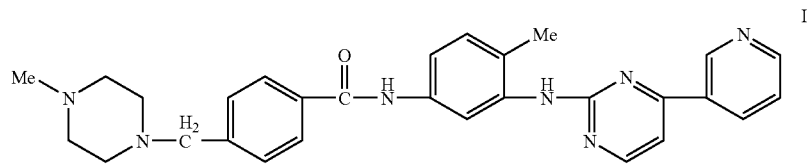

and its salts, particularly the imatinib mesylate, are one of the more commonly used chemotherapeutic agents used for the treatment of Philadelphia chromosome positive chronic myeloid leukemia in blast phase, accelerated phase or chronic phase. This compound has been associated with debilitating side effects such as hepatotoxicity and hematologic toxicity, edema, nausea, vomiting, diarrhea, muscle cramps, musculoskeletal pain and rash. By monitoring the levels of imatinib, its salts or its pharmacologically active metabolites in the body and adjusting the dose, these side effects can be better controlled and limited in patients (Gleevec package insert, Novartis Pharmaceuticals Corporation, East Hanover, N.J., July 2004).

The preferred salt of imatinib is imatinib mesylate which has the formula:

Since imatinib has been associated with debilitating side effects, by monitoring the levels of this chemotherapeutic agent in the body and adjusting the dose, these side effects can be better controlled and limited in patients.

When administering imatinib or its salts to patients, there is often high variable relationship between the dose of imatinib or its salt, and the resulting serum drug concentration of these chemotherapeutic agents or their chemotherapeutically active metabolites, that affects the degree of clinical effectiveness and toxicity. The degree of intra- and inter-individual pharmacokinetic variability of imatinib and its salts has been reported to be four fold (See Gleevec package insert, Novartis Pharmaceuticals Corporation, East Hanover, N.J., July 2004, Pindolia et.al. Pharmacotherapy, 22:1249-1265, 2002) and is impacted by many factors, including:

Organ function
Genetic regulation
Disease state
Age
Drug-drug interaction
Time of drug ingestion
Compliance As a result of this variability, equal doses of the same drug in different individuals can result in dramatically different clinical outcomes. The effectiveness of the same imatinib or its salts dosage varies significantly based upon individual drug clearance and the ultimate serum drug concentration in the patient. Therapeutic drug management would provide the clinician with insight on patient variation in drug administration. With therapeutic drug management, drug dosages could be individualized to the patient, and the chances of effectively treating the cancer without the unwanted side effects would be much higher.

In addition, therapeutic drug management of imatinib or its salts would serve as an excellent tool to ensure compliance in administering chemotherapy with the actual prescribed dosage and achievement of the effective serum concentration levels. Routine therapeutic drug management of imatinib or its salts would require the availability of simple automated tests adaptable to general laboratory equipment.

The use of liquid chromatography (LC)-tandem mass spectroscometry to determine the concentration of imatinib,

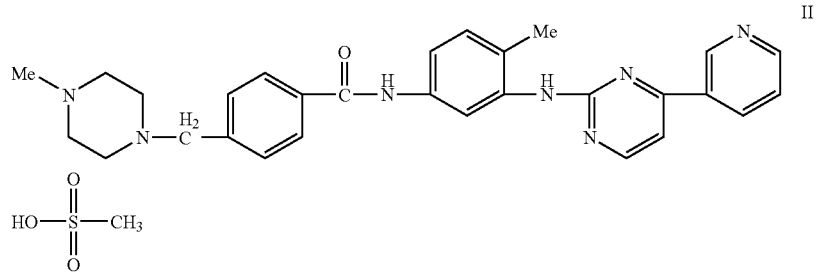

imatinib salts or their chemotherapeutic metabolites in human blood and plasma has been described (Guetens, J Pharm Biomed Anal., 33(5):879-89 2003; Bakhtiar, J Chromatrography B, 768(2):325-340, 2002; Titier, Ther. Drug. Monit., (27)5:634-640, 2005). A LC method to determine the purity of imatinib, imatinib salts or their chemotherapeutic metabolites (Vivekanand, J Pharm Biomed Anal., 28(6):1183-94, 2002) has also been developed but was not used to determine levels in biological fluids. These methods are labor intensive, use expensive equipment and are not amenable to routine clinical laboratory use.

Assay conditions have been described to monitor the activity of protein tyrosine kinases using ATP, where the phosphorous is labeled with a $P^{32}$ radioactive isotope in a variety of formats including scintillation proximity, solid phase, filtration and radio-autographic assays (Evans et.al., J Biochem Biophys Methods, 50:151-161, 2002; Park et.al., Anal Biochem., 269:94-104, 1999; Witt et.al., Anal Biochem., 66:253-258, 1975; Braunwalder et. al., Anal Biochem., 234:23-26, 1996; Schaefer et. al., Anal Biochem., 261:100-112, 1998). Non-radio-isotopic assays have also been developed using enzyme-linked immunosorbent (ELISA), fluorometric, fluorescent polarization formats (Yamato et. al., Anal Biochem., 315:256-261, 2003; Angles et. al., Anal Biochem., 236: 49-55, 1996; Braunwalder et. al., Anal Biochem., 238:159-164, 1996; Seethala et. al. Anal Biochem., 255:257-262, 1998; Barker, Biochem., 34(45): 14843-51, 1995).

These methods were developed to either screen for protein tyrosine kinase activity in biological extracts or for screening potential new inhibitors of the tyrosine kinases. In addition these methods are not amenable for use on routine clinical analyzers. Furthermore, they do not provide a method to directly quantitate imatinib, its salts or their thereapeutically active metabolites, in the patients plasma or serum for the purpose of therapeutic drug monitoring.

SUMMARY OF THE INVENTION

It has been found that the activity of the abl tyrosine kinase enzymes, preferably bcr-abl protein tyrosine kinase and v-abl protein tyrosine kinase, is inhibited by certain analytes particularly imatinib, its salts and their pharmacologically active metabolites. Therefore, in accordance with this invention, it has been discovered that the abl tyrosine kinase enzymes, preferably bcr-abl protein kinase and v-abl protein or mixtures thereof, can be used in a substrate to carry out an efficient and effective enzymatic assay for determining the presence of and/or quantifying the amount of analytes which inactivate these abl protein tyrosine kinase enzymes, particularly imatinib, salts thereof or the pharmacologically active metabolites in human patient samples, particularly, liquid human patient samples such as blood serum or plasma.

In addition, this enzymatic assay can be utilized to detect and quantify the presence of any pharmacologically active compound, particularly chemotherapeutic agents which inhibit abl protein-tyrosine kinase enzymes. The use of enzymatic assays provides a simple and economic method which is amenable for use in analysis to both detect and quantify these analytes, particularly imatinib, its salts or their metabolites in human patient samples, utilizing ordinary laboratory experiments for purposes of therapeutic drug monitoring.

Also in accordance with this invention, a kit is provided for detecting and quantifying these analytes such as imatinib, its salts or its pharmacologically active metabolites in patient samples for the purpose of therapeutic drug monitoring.

DETAILED DESCRIPTION OF THE INVENTION

In accordance with this invention, an enzymatic assay for detecting the presence of the analytes which inactivate these abl protein tyrosine kinase enzymes particularly analytes such as imatinib, imatinib salts or pharmacologically active metabolites thereof, in the patient samples by utilizing the properties of the abl protein tyrosine kinase enzymes preferably bcr-abl protein tyrosine kinase or v-abl protein-tyrosine kinase, to be inactivated by the analytes particularly imatinib, imatinib salts or their pharmacologically active metabolites. It is through this property that the enzymatic assay for detecting the presence of these analytes, particularly chemotherapeutic agents, in bloodstreams for therapeutic drug monitoring is achieved.

In accordance with this invention, enzymatic assays for either determining the presence or quantitating the amount of the analytes, particularly the above chemotherapeutic agents, which inactivate these abl protein tyrosine kinase enzymes is achieved by first forming in an aqueous medium a mixture containing a human sample for determination of the analytes, particularly the aforementioned chemotherapeutic agents, the abl protein tyrosine kinase enzyme, preferably v-abl protein-tyrosine kinase for bcr-abl protein tyrosine kinase or mixtures thereof and a polypeptide substrate containing NADH. The polypeptide substrate, in accordance with this invention, should be capable of converting NADH to NAD through the use of abl protein tyrosine kinase. In accordance with a preferred embodiment of this invention, the polypeptide substrate is a protein substrate capable of converting NADH to NAD through the use of abl protein tyrosine kinase enzymes. The aforementioned mixture is incubated under conditions which can cause the analytes, particularly the chemotherapeutic agent, in the sample, to react with the enzyme. After incubation the amount of NADH in the substrate, which is converted to NAD, is measured. By use of this enzymatic assay, the presence and amounts of these analytes in body fluid samples, preferably blood or plasma samples, can be detected and/or quantified. In this manner, a patient being treated with a pharmaceutically active material which deactivates abl protein tyrosine kinase enzymes such as imatinib or salts thereof can be monitored during drug therapy and their treatment adjusted in accordance with the results of said monitoring. By means of this invention one achieves the therapeutic drug management of such pharmaceutically active materials particularly imatinib and its salts in cancer patients being treated with imatinib or its salts as a chemotherapeutic agent.

The presence of the analytes, particularly imatinib, imatinib salts and pharmacologically active metabolites of imatinib or its salts, can be detected through the conversion of NADH to NAD, which conversion is inhibited by the presence of these analytes in the patient sample. The presence of NADH can be measured optically by monitoring the change in absorption, preferably at a wave length of 340 nm, i.e., the characteristic absorption region of NADH, and this change in absorption can be correlated with the presence and the amount of the aforementioned chemotherapeutic agents in the patient sample which inhibit the enzymatic reaction which causes the conversion of NADH to NAD. Therefore, the amount of NADH present after incubation will be directly proportional to the amount of the aforementioned chemotherapeutic agents in the sample. Generally the amount of these chemotherapeutic agents, in a sample, is determined by correlating the measured amount of NADH in the presence of these chemotherapeutic agents in the sample with values of NADH determined from standard or calibration curve samples containing known amounts of agents which known amounts are in the range expected for the sample to be tested. These studies for producing calibration curves are determined using the same enzyme assay procedure as used for the sample.

In accordance with this invention, the preferred polypeptide substrate is a protein substrate containing NADH which is capable of converting NADH to an NAD by means of an abl protein-tyrosine kinase, preferably v-abl protein-tyrosine kinase, bcr-abl protein-tyrosine kinase or mixtures thereof contains adenosine triphosphate [ATP], a tyrosine containing polypeptide, preferably a protein, capable of phosphorolation by tyrosine kinase, phosphoenol pyruvate [PYK] and lactate dehydrogenase [LD]. In accordance with this preferred substrate, the ATP is converted to the NAD by the following series of reactions:

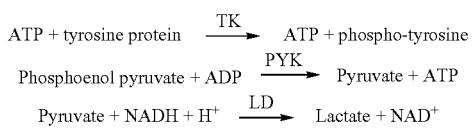

In this reaction scheme, TK represents the abl protein-tyrosine kinase enzyme which can be preferably v-abl protein-tyrosine kinase, or bcr-abl protein-tyrosine kinase whose activity is inhibited by imatinib, its salt or their active metabolites. The ATP binding site of the enzyme TK is inhibited by the presence in the sample of the analyte so that this reaction sequence does not produce ADP and in turn the NADH is not converted to NAD+.

In accordance with this invention, the polypeptide substrate containing NADH, which is capable of converting NADH to NAD by means of these enzymes, can be used to determine the presence in human samples of any chemotherapeutic agent that is capable of inactivating the abl protein-tyrosine kinase enzymes. In addition, these enzymes are deactivated by the pharmacologically active metabolites produced by imatinib or imatinib salts which can be present in the patient samples. By being reactive with these metabolites, this enzyme assay produces an accurate and effective means for monitoring the drug therapy through the presence of analytes particularly imatinib, imatinib salts or their pharmacologically active metabolites in the bloodstream of patients. The term pharmacologically active designates those metabolites of imatinib, or imatinib salts which act in a similar fashion as chemotherapeutic agents as imatinib or imatinib salts.

The abl protein tyrosine kinase enzymes including the bcr-abl protein tyrosine kinase and v-abl protein tyrosine kinase are known enzymes obtained from chronic myeloid leukemia cells such as ATCC CCL243. The enzyme bcr-abl protein tyrosine kinase has been described in WO 03/031608 and U.S. Patent Publication 2003/070851 A1, published Sep. 11, 2003. Its purification and characterization from chronic myeloid leukemia cells is set further in O'Hare et al., Blood, 108(8):2532-2539, 2004 and Corbin et al., J. Biol. Chem., 277(35):32214-33219, 2004. The enzyme v-abl protein tyrosine kinase is a commercially available enzyme from Calbiochem and New England Biolabs.

The enzyme assay of this invention is carried out with patient samples suspected of containing imatinib, imatinib salts and/or pharmacologically active metabolites thereof. Any sample that is reasonably suspected of containing this chemotherapeutic agent can be analyzed by the method of the present invention. The sample is typically an aqueous solution such as a body fluid from a human patient for example, urine, whole blood plasma, serum, saliva, semen, stool, sputum, cerebral spinal fluid, mucous or the like, but preferably blood plasma or serum. The sample can be pretreated if desired and prepared in any convenient medium that does not interfere with the assay. It is preferred that the sample be supplied in an aqueous medium since this assay is preferably carried out in an aqueous medium.

The enzymatic assay is carried out by forming, in an aqueous medium, the mixture containing the sample suspected of containing the aforementioned chemotherapeutic agents with the abl protein tyrosine kinase enzyme, preferably v-abl protein tyrosine kinase, ber-abl protein tyrosine kinase or mixtures thereof and a polypeptide substrate containing NADH. The polypeptide substrate for use in this invention is one that is capable of converting NADH to NAD by means of the above abl protein tyrosine kinase enzymes. Any polypeptide substrate which is capable of converting NADH to NAD by means of these enzymes can be utilized in accordance with this assay.

The preferred substrate comprises the following co-enzymes:
  a) lactate dehydrogenase; and
  b) pyruvate kinase;

as well as a polypeptide substrate for the co-enzyme which together with the abl protein tyrosine kinase enzymes particularly bcr-abl protein tyrosine kinase and/or v-abl protein tyrosine kinase react with ATP to cause the conversion of NADH into NAD. This substrate generally comprises the tyrosine containing polypeptide capable of phosphorolation by tyrosine kinase, phosphoenol pyruvate and adenosine triphosphate (ATP). In accordance with this invention any tyrosine containing polypeptide, which includes proteins, capable of phosphorolation by tyrosine kinase, such as ovalbumin, "Abl Peptide Substrate" from New England BioLabs, Abltide, from Upstate Biotechnology, casein, polypeptides of glutamic acid and tyrosine and bovine serum albumin, can be utilized as the tyrosine containing polypeptide in the polypeptide substrate. The preferred tyrosine containing polypeptide in this substrate is a tyrosine containing protein capable of phosphorolation such as bovine serum albumin and casein.

In the next step of performing the assay, the aqueous mixture of NADH, the sample, substrate and the abl protein tyrosine kinase enzyme, together with the co-enzymes are incubated in the aqueous medium in order to allow any of the analyte in the sample, particularly imatinib, imatinib salts and/or pharmacologically active metabolites thereof which may be present in the sample to react with the abl protein tyrosine kinase enzymes. Incubation can take place by simply mixing the reagents and the sample in the aqueous medium. In any event, temperature and pressure are not critical in carrying out the incubation step which will allow the presence of the chemotherapeutic agent in the sample to be detected through the use of the reagents. In carrying out this reaction temperatures of from 10° C. to 40° C. are generally utilized.

The pH at which the method of the present invention is conducted is not critical and can range from 4 to 11, more usually in the range of 5 to 10, and most preferably in the range of from about 6 to 8. Various buffers can be used to achieve and maintain a pH during the assay procedure. Representative buffers include borate, phosphate, carbonate, Tris, barbital and the like. The particular buffer used is not critical to the present invention but the Tris and phosphate buffers are preferred.

The amount of the imatinib active ingredients in the patient sample can be measured by measuring the rate of conversion of the NADH in the sample converted to NAD. Any conventional means of measuring the conversion of NADH to NAD may be used for carrying out the assay. In accordance with one embodiment of this invention the rate of formation of ADP is measured by the monitoring the disappearance of NADH spectrophotometrically at the aforementioned wavelengths, preferably at a wavelength of 340 nm which is the characteristic absorption region of NADH (Roon et. al. Meth Enzymol., 174:317, 1970; Roon et. al., J Biol. Chem., 247:4107, 1972; Roon et. al., J Biol. Chem., 247:7539, 1972). The concentration of the chemotherapeutic agents in this sample, which is subjected to the aforementioned assay, is directly proportional to the absorption of NADH. In like manner, the assay of the present invention may be used to determine levels of other abl protein kinase inhibitors which include other chemotherapeutic agents.

In performing the assay in accordance with this invention a measured amount of sample suspected of containing the analyte which inhibits the enzyme abl protein tyrosine kinase is used together with known concentrations of the enzymes, co-enzymes, peptide substrates and NADH. In this way the mixture is formed with known or predetermined amounts of the various components so that calibration and quantification to determine the amount of the analyte in the sample can be achieved. In this manner, accurate measurements of the amount of the analyte in the sample can be determined.

In accordance with a preferred embodiment of this invention, the determination of imatinib, imatinib salts and chemotherapeutically active metabolites thereof by the assay of this invention, may be conducted by a rate-assay method wherein change in absorbance of NADH per unit time is measured or by an end-point method wherein the reaction is quenched after a certain period of time has elapsed. The method can easily be applied to automated analyzers for laboratory or clinical analysis.

Calibration material means any standard or reference material containing a known amount of the analyte, i.e., imatinib, imatinib salts or their pharmacologically active metabolites, to be measured. The sample suspected of containing this analyte and the calibration material are assayed under similar conditions. Analyte concentration is then calculated by comparing the results obtained for the unknown specimen with results obtained for the standard. This is commonly done by constructing a calibration curve plotting the concentration of drug versus absorbance at 340 nm.

Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumin, or surfactants, particularly non-ionic surfactants, or the like.

Any sample that is reasonably suspected of containing the analyte, i.e., imatinib salts or active metabolites thereof or other inhibitors of abl protein-tyrosine kinase enzymes preferably bcr-abl protein-tyrosine kinase or v-abl protein-tyrosine kinase, can be analyzed by the method of the present invention. The sample is typically an aqueous solution such as a body fluid from a host, for example, urine, whole blood, plasma, serum, saliva, semen, stool, sputum, cerebral spinal fluid, tears, mucus or the like, but preferably is plasma or serum. The sample can be pretreated if desired and can be prepared in any convenient medium that does not interfere with the assay. An aqueous medium is preferred.

Measuring the amount of analyte can be by quantitative, semi-quantitative and qualitative methods as well as all other measuring methods are considered to be methods of measuring the amount of analyte. For example, a method that merely detects the presence or absence of the analyte in a sample suspected of containing imatinib, salts and active metabolites thereof is considered to be included within the scope of the present invention. The terms "detecting" and "determining", as well as other common synonyms for measuring, are contemplated within the scope of the present invention.

Another aspect of the present invention relates to kits useful for conveniently performing the assay methods of the invention for the determination of this analyte. To enhance the versatility of the subject invention, reagents useful in the methods of the invention can be provided in packaged combination, in the same or separate containers, in liquid or lyophilized form where the reagents are present in a predetermined amount which provides for substantial optimization of the method and assay. The reagents may each be in separate containers or various reagents can be combined in two or more containers depending on the cross-reactivity and stability of the reagents. The kit of the present invention contains the reagents, which are abl protein tyrosine kinase, PYK and LH enzymes, polypeptide (phosphate accepter) ATP, NADH, phosphoenol pyruvate (PEP) substrates and various cofactors that optimize the reaction. The enzymes and polypeptide substrate are commonly combined with an appropriate buffer and ancillary materials and then packaged and the other substrates are combined to make the second reagent. The reagents may remain in liquid form or lyophilized. The kit can further comprise other packaged calibration materials.

The kit of this invention is composed of the following reagents:
 a) the abl protein kinase enzyme;
 b) NADH; and
 c) the polypeptide substrate capable of converting NADH to NAD by means of the abl protein kinase.

In this kit the abl protein kinase enzyme should be packaged in separate containers from the necessary active compound in the substrate which in this case is ATP. However, the NADH and the substrate and co enzymes can be packaged in one or separate containers. In fact, each of the reagents of the substrate may be packaged in separate containers or with the abl protein kinase enzyme provided that the active component of the substrate, ATP, is packaged separately from the active compound.

In accordance with the preferred embodiment of this invention, the kit comprises the following reagents:
 a) the enzyme component containing abl protein kinase;
 b) a tyrosine containing polypeptide capable of phosphorolation by tyrosine kinase;
 c) pyruvate kinase;
 d) lactate dehydrogenase;
 e) phosphoenol pyruvate;
 f) NADH; and
 g) ATP.

In this embodiment the active compound in the substrate is ATP. Therefore, the ATP reagent must be kept in a separate container from one or more of the containers containing the abl protein kinase enzyme reagent. In this manner, the kit must contain at least two separate containers.

When a kit contains two separate containers, the kit contains one container containing ATP and the other container containing reagents a), b), c), d), e) and f). In accordance with another embodiment, the kit contains three containers, one containing ATP, the other container containing reagents b), c), d), e), f) and g) and the third container containing the abl protein kinase enzyme reagent.

If the containers contain the reagents in an aqueous liquid medium, the kits should set forth the concentration of each of the reagents in each of the containers. The concentration of the reagents, including the enzymes, co-enzymes, protein substrates and NADH, are important for quantitating the amount of the analyte, i.e., preferably imatinib, imatinib salts and/or their active metabolites in the sample. If the components in the containers are in powder form then the weight of each of the reagents contained in the container should be set forth either on the package, container or package insert. In this manner, predetermined amounts and/or concentrations of the reagents necessary for carrying out the enzymatic assay of this invention are supplied with the kit. The necessary reagents for carrying the enzymatic assay of this invention can also be packaged with conventional buffers and stabilizers to achieve and maintain the proper pH during the assay procedure. Representative buffers include borate, phosphate, carbonate, Tris, barbital and the like. The particular buffer used is not critical to the invention but the Tris and phosphate buffers are preferred. In accordance with this invention the necessary reagents for carrying out the enzymatic assay may be present in the containers in liquid or lyophilized form.

The kit can further comprise other packaged calibration and/or control material. These calibration and/or control material are any standard or referenced material containing a known amount of analyte. In accordance with the preferred embodiment of this invention one or more separate containers are supplied containing samples with known amounts of the analyte to be measured. While one sample with known amounts of the analyte to be measured can be used, generally, it is preferred to have from three to five separate control materials or samples containing known or predetermined amounts of the analyte, each at different concentrations. In this manner, a curve can be obtained. The concentration of the analyte is calculated by comparing the results from the unknown sample with the results obtained from the standard. In carrying out the calibration of the standard in the measured amount of the analyte the assay is done utilizing the same conditions and amounts as used in assaying the sample containing the unknown amount of analyte.

EXPERIMENTAL

A more complete understanding of the present invention will be obtained by reference to the following non-limiting examples.

Experimental Abbreviations
ATP Adenosine triphosphate
BSA Bovine serum albumin
DTT Dithiothreitol
EDTA Ethylene diaminetetraacetic acid
LH Lactate dehydrogenase
$MgSO_4$ Magnesium sulfate
NADH Nicotinamide adenine dinucleotide reduced
PEP Phosphoenol pyruvate
PYK Pyruvate kinase
KCl Potassium chloride
TK abl tyrosine kinase
TRIS 2-Amino-2-(hydroxymethyl)-1,3-propanediol In the examples below, three reagents were prepared, the first comprising the two enzymes PYK and LH with bovine serum albumin (BSA), PEP and NADH and second TK and the third reagent comprising ATP, PEP, PYK, LH and NADH. In the examples, BSA was combined with the first reagent containing PYK and LH due to the known stabilizing effects of BSA on enzymes; however, alternatively the BSA could be incorporated in the substrate reagent bottle instead. Other combinations and perturbations may also suggest themselves to those skilled in the art.

EXAMPLE 1

Expression and Purification of GST-abl Kinase

Cells of a\bacterial strain, BL21 (DE3) LysS expressing GST-abl kinase, were grown in 3 L LB, 100 ug/ml ampicillin to OD600=0.5 at 28° C. and induced with 0.5 mM IPTG for 20 h. (Foulkes et. al. J. Biol Chem 260(13), pp 8070-8077, 1985 al. Oncogene 15, pp 2249-2254, 1997).

Cells were harvested by centrifugation and resuspended in D-PBS w/o $Ca^{2+}/Mg^{2+}$ containing 0.4% Triton-X-100 (buffer A). Cells were then lysed by sonication in the presence of complete EDTA-free protease inhibitor cocktail (Roche). The lysate was clarified by centrifugation for 30 min at 35,000×g. and subsequent filtration through 0.22 μm cellulose acetate membranes (Corning).

GST-abl kinase was purified via FPLC (Amersham Biosciences) using a 1 mL GSTRAP HP column. After equilibration of the column with buffer A, the lysate (~300 ml) was loaded overnight at a flow rate of 0.22 mL/min. The column was washed consecutively 10 volumes each of buffer A and buffer B (D-PBS w/o $Ca^{2+}/Mg^{2+}$). The protein was eluted with buffer C (100 mM Tris pH 8.0, 150 mM NaCl, 30 mM reduced glutathione), supplemented with 1 volume of 80% glycerol, and stored at −20° C.

EXAMPLE 2

Detection of Imatinib Mesylate Inhibition of Tyrosine Kinase by using a Coupled Enzyme Reaction To detect the inhibition of TK by imatinib mesylate in a sample the following three reagents were mixed in a microcuvette (1 per sample replicate) and incubated at 37 C. with sample. Addition of reagents, incubation of cuvettes and monitoring of reactions by absorbance readings at 340 nm were accomplished with an automated benchtop clinical analyzer (COBAS MIRA, Roche Diagnostics Corp., Indianapolis). This analyzer was used for the convenience of automation. The assay could also be accomplished by manual addition to any cuvette, which allowed mixing, incubation at 37 C. and that could be measured at 340 nm in a spectrophotometer.

The first reagent containing the enzymes PK (141 units, 0.024 mg/mL), LH (74.6 units, 2.98 units/mL) and the substrate PEP (0.78 mg/mL) in a buffer comprised of 50 mM Tris, 20.8 mg/mL BSA, 200 mM DTT, 144 uM EDTA, 52 mM KCl, 9 mM $MgSO_4$, pH 8. 150 uL of the first reagent were added to the microcuvette. After this reagent had incubated at 37 C. for 25 seconds the sample containing imatinib mesylate (dissolved in 50 mM TRIS buffer pH 8) was added. For the addition of sample 20 uL of diluent (50 mM TRIS, pH 8) were aspirated into the analyzer's sample needle, followed by 10 uL of sample. Sample and diluent were dispensed together into the microcuvette, and were then mixed. No reaction occurs at this time point, as there is no TK present in the reaction mixture. After an additional 25 second incubation at 37 C. 25 uL of TK reagent (0.5 mg/mL TK in 50 mM TRIS buffer, 1.05 mg/mL BSA, 100 uM DTT, 54 uM KCl, 8.3 uM $MgSO_4$, 0.14 uM EDTA, pH 8) was added with 25 uL of diluent (50 mM TRIS, pH 8), after addition the contents of the microcuvette were mixed. The mixture was incubated for an additional 25 seconds at 37 C. No reaction yet takes place as there is no ATP in the mixture. Following the incubation reagent 3 is added: 3.4 mg of ATP in reagent 1 above. 25 uL of reagent 3 were added with 25 uL of diluent followed by mixing. The conversion of ATP to ADP by TK occurs in the reaction cuvette. In the presence of ADP phosphoenol pyruvate is converted to pyruvate by PK. In the presence of the pyruvate generated by the PK enzyme reaction LD reduces NADH to NAD.

NADH absorbs at 340 nm, and its disappearance was monitored at this wavelength by taking readings every 25 seconds for 1,175 seconds. The rate of the reaction per minute as change in absorbance-340 nm per unit time was calculated from the slope of absorbance vs. time.

EXAMPLE 3

Standard Curve with Imatinib Mesylate

Standards containing imatinib mesylate were prepared as follows. To 4.5 mL of a phosphate buffer (50 mM, pH 5.4) 1.8 mg of imatinib mesylate (Sequoia Research Products Ltd, England) was added. This solution was diluted 1:100 (20 μL in 1.88 mL) into tris buffer (50 mM, pH 8.0) to yield a 4000 ng/mL solution. This solution was subsequently diluted to yield standards of 4000, 1000, 500, 250 and 125 ng/mL. These standards were measured as samples in example 2. The change in absorbance (rate) for each standard was plotted versus concentration of the drug. The amount of drug is inversely proportional to the concentration of NAD+ or directly proportional to the concentration of NADH. Concentrations of imatinib mesylate are calculated by comparing the rate of reduction of NADH in an unknown sample with the rate of reduction of NADH by the standards containing known amounts of imatinib mesylate.

Typical results of a standard curve are shown in Table 1.

TABLE 1

Standard curve of Imatinib mesylate

| Drug Concentration ng/mL | Rate mA/min × −100 |
| --- | --- |
| 0 | 682 |
| 125 | 650 |
| 250 | 641 |
| 500 | 627 |
| 1000 | 617 |
| 4000 | 539 |

In addition, other modifications may be made to adapt a particular situation, material, composition of matter, process, process step or steps, to the objective, spirit and scope of the present invention.

What is claimed is:

1. An enzymatic assay for determining the amount in a human blood serum or plasma sample of a chemotherapeutic agent selected from the group consisting of imatinib and chemotherapeutically active metabolites thereof comprising:
   a) forming in an aqueous medium a mixture containing said sample suspected of containing said chemotherapeutic agent with NADH; an abl protein tyrosine kinase which is inhibited by said chemotherapeutic agent; lactate dehydrogenase in an amount effective to convert NADH in the mixture to NAD; ATP; phosphoenol pyruvate; pyruvate kinase; and a tyrosine-containing polypeptide capable of being phosphorylated by an abl protein tyrosine kinase;
   b) incubating said mixture under conditions which cause said chemotherapeutic agent in the sample to react with said abl protein tyrosine kinase;
   c) thereafter measuring the rate at which the NADH is converted to NAD; and
   d) quantifying the amount of the chemotherapeutic agent in the sample based upon said rate.

2. The enzymatic assay of claim 1, wherein said abl protein tyrosine kinase is selected from v-abl protein tyrosine kinase, bcr-abl protein tyrosine kinase or a mixture thereof.

3. The enzymatic assay of claim 1, wherein said abl protein tyrosine kinase is v-abl protein tyrosine kinase, bcr-abl protein tyrosine kinase or a mixture thereof.

4. The enzymatic assay of claim 3, wherein said tyrosine containing polypeptide capable of being phosphorylated is bovine serum albumin.

5. The enzymatic assay of claim 1, wherein the amount of chemotherapeutic agent in said sample, is quantified by comparing the measured rate of conversion of NADH to NAD in the sample with the rate of conversion of NADH to NAD in one or more samples containing known amounts of said chemotherapeutic agent utilizing the same assay.

6. The enzymatic assay of claim 5, wherein said abl kinase enzymes are v-abl protein tyrosine kinase, bcr-abl protein tyrosine kinase or a mixture thereof.

7. The enzymatic assay of claim 6, wherein said tyrosine containing polypeptide capable of being phosphorylated is bovine serum albumin.

8. A kit for conducting an enzymatic assay to quantify in a human blood serum or plasma sample, the amount of a chemotherapeutic agent selected from the group consisting of imatinib and chemotherapeutically active metabolites thereof comprising
   1) at least two separate reagent containers containing a predetermined amount of the following reagents:
      a) a first enzyme component containing an abl protein tyrosine kinase which is capable of being inhibited by said chemotherapeutic agent;
      b) pyruvate kinase;
      c) a tyrosine-containing polypeptide capable of being phosphorylated by said abl protein tyrosine kinase;
      d) lactate dehydrogenase;
      e) phosphoenol pyruvate;
      f) NADH; and
      g) ATP;
   wherein ATP is in a separate reagent container from the one or more reagent containers containing the first enzyme component; and 2) one or more separate non reagent containers, with each said non reagent container containing a sample having a different predetermined amount of the chemotherapeutic agent to be quantified.

9. The kit of claim 8, wherein said abl protein tyrosine kinase is v-abl protein tyrosine kinase, bcr-abl protein tyrosine kinase or a mixture thereof.

10. The kit of claim 9, wherein the reagents are present in the reagent containers in an aqueous medium containing a buffer and a stabilizer.

11. The kit of claim 10, wherein the reagents are present in two separate reagent containers, one of said reagent containers containing ATP, the other reagent container containing reagents b), c), d), e), f) and the first enzyme component of reagent a).

12. The kit of claim 10, wherein the reagents are present in three separate reagent containers, one reagent container containing ATP, the second reagent container containing the first enzyme component and the third reagent container containing the reagents of b), c), d), e) and f).

13. The kit of claim 8, wherein said tyrosine-containing polypeptide capable of being phosphorylated is bovine serum albumin.

14. The kit of claim 13, wherein said abl protein tyrosine kinase is v-abl protein tyrosine kinase, bcr-abl protein tyrosine kinase or a mixture thereof.

15. The kit of claim 14, wherein the reagents are present in the reagent containers in an aqueous medium containing a buffer and a stabilizer.

16. The kit of claim 14, wherein the reagents are present in two separate reagent containers, one of said reagent containers containing ATP, the other reagent container containing reagents b), e), d), e), f), g) and the first enzyme component of reagent a).

17. The kit of claim 14, wherein the reagents are present in three separate reagent containers, one reagent container containing ATP, the second reagent container containing the first enzyme component and the third reagent container containing the reagents of b), c), d), e) and f).

* * * * *